United States Patent
Rehkemper

(10) Patent No.: US 7,270,129 B1
(45) Date of Patent: *Sep. 18, 2007

(54) DENTAL FLOSSER

(75) Inventor: Steven Rehkemper, Chicago, IL (US)

(73) Assignee: Rehco, LLC, Chicago, IL (US)

( * ) Notice: Subject to any disclaimer, the term of this patent is extended or adjusted under 35 U.S.C. 154(b) by 319 days.

This patent is subject to a terminal disclaimer.

(21) Appl. No.: 10/876,437

(22) Filed: Jun. 28, 2004

Related U.S. Application Data

(63) Continuation-in-part of application No. 10/795,752, filed on Mar. 8, 2004, and a continuation-in-part of application No. 10/781,960, filed on Feb. 20, 2004.

(51) Int. Cl.
*A61C 15/00* (2006.01)
(52) U.S. Cl. .................................................. 132/322
(58) Field of Classification Search ........ 132/322–329; 15/185, 172, 144.1–144; 16/429, 438, 900; 279/155
See application file for complete search history.

(56) References Cited

U.S. PATENT DOCUMENTS

| | | | |
|---|---|---|---|
| 664,126 A * | 12/1900 | Cowan | 132/325 |
| 677,947 A * | 7/1901 | Cowan | 132/324 |
| 3,421,524 A | 1/1969 | Waters | |
| 4,014,354 A | 3/1977 | Garrett | |
| 4,020,521 A * | 5/1977 | Velasquez | 15/172 |
| 4,235,253 A | 11/1980 | Moore | |
| 4,307,740 A | 12/1981 | Florindez et al. | |
| 4,794,663 A * | 1/1989 | Vosbikian | 15/229.6 |
| 4,830,032 A | 5/1989 | Jousson | |
| 4,880,382 A | 11/1989 | Moret et al. | |
| 5,093,991 A * | 3/1992 | Hendrickson | 30/531 |
| 5,165,135 A * | 11/1992 | Su | 15/167.1 |
| 5,170,809 A | 12/1992 | Imai et al. | |
| 5,323,796 A | 6/1994 | Urso | |
| 5,343,883 A | 9/1994 | Murayama | |
| 5,423,427 A * | 6/1995 | Brown | 206/581 |
| 5,581,838 A * | 12/1996 | Rocco | 15/110 |
| RE35,712 E * | 1/1998 | Murayama | 132/322 |
| 6,189,222 B1 * | 2/2001 | Doyle | 30/531 |
| 6,571,804 B2 * | 6/2003 | Adler | 132/325 |
| 6,997,191 B2 * | 2/2006 | Nudo, Sr. | 132/328 |
| 2003/0111091 A1 * | 6/2003 | Hotta et al. | 132/322 |
| 2004/0079384 A1 | 4/2004 | Lai et al. | |

* cited by examiner

*Primary Examiner*—Todd E. Manahan
*Assistant Examiner*—Rachel A. Running
(74) *Attorney, Agent, or Firm*—Adam K Sacharoff; Much Shelist

(57) ABSTRACT

In one embodiment of the present invention, an electric folding flossing apparatus is provided and includes a handle and a power supply contained therein, an arm movably joined to the handle at one end and having a flossing tool disposed at another end, a motor mechanism contained within the arm and operable to move the flossing tool when activated, and includes the ability to supply power to the motor mechanism when the flossing tool is in an outstretched position. The ability to supply power to the motor mechanism is accomplished with a first electrical contact in communication with the power supply and positioned in the handle, and a second electrical contact in communication with the motor mechanism and positioned in the arm such that when the arm and the handle are in the outstretched position the first and second electrical contacts make an electrical connection such that power from the power supply operates the motor mechanism.

20 Claims, 9 Drawing Sheets

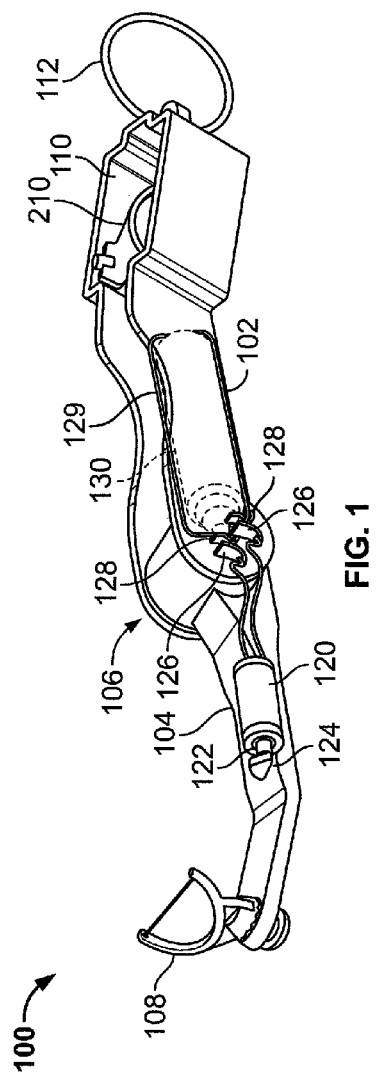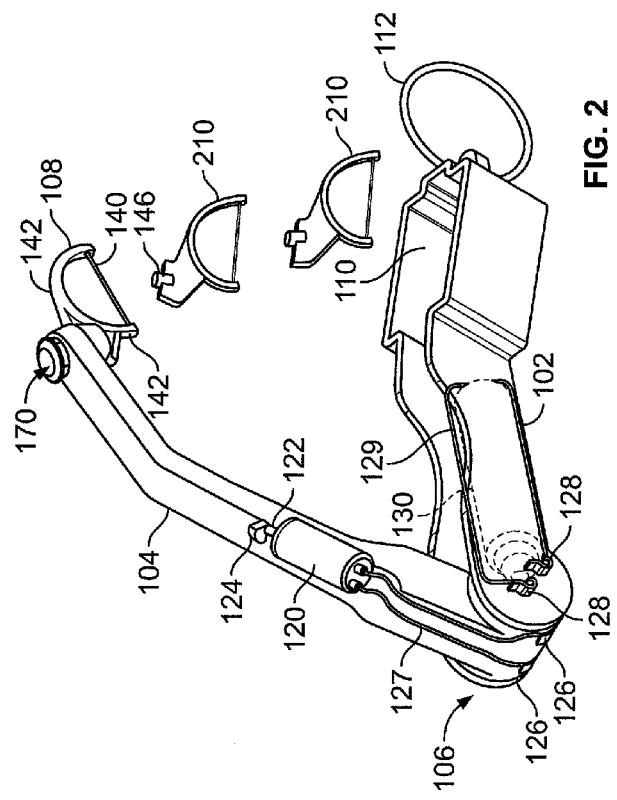

DENTAL FLOSSER

CROSS REFERENCE TO RELATED APPLICATIONS

This application is a continuation in part of Ser. No. 10/795,752 filed Mar. 8, 2004 and a continuation in part of Ser. No. 10/781,960 filed Feb. 20, 2004.

FIELD OF THE INVENTION

The present invention relates to flossing tools used to clean between teeth and particularly to an electric flosser that includes a head that vibrates.

BACKGROUND OF THE INVENTION

Flossers both electric and non-electric are known in the industry and in the prior art. Numerous patents have issued throughout the years to cover various improvements and novel features in the flosser industry. For example, U.S. Pat. No. 5,170,809 requires a dental floss to be reciprocated along an axis substantially parallel to the axis of a handle (if the dental floss apparatus is positioned upright, the floss would be moving in an up and down motion), or that the motor mechanism moved a shaft in the handle only along the handle's longitudinal axis, which would impart the same movement in the dental floss attached to the shaft (again, the motion would be an up and down motion if the apparatus is standing in an upright position). U.S. Pat. RE 35,712 discloses a sonic dental device that includes a flossing head that stores extra dental floss such that a user may exchange used dental floss with new floss. U.S. Pat. No. 5,323,796 is directed to an automated dental flosser that includes a twine of floss held in the body of the device for which a user may dispense unused floss. However, prior art flossing apparatuses seem to lack the ability to provide a compact electric flosser suitable for travel or provide an electric flosser that permits the flossing head to rotate 360° such that the user has the ability to change the angle of the flossing head, especially during use.

The present invention overcomes these shortcomings by providing in a first embodiment a folding electric flosser and in a second embodiment an electric flosser that includes a rotatable flossing head.

SUMMARY OF THE INVENTION

In accordance with an embodiment of the present invention a folding electric flosser is provided. The flosser contains a handle and an arm movably joined to the handle, which includes a disposable flossing head disposed at one end. The flosser has a power supply contained within the handle and a motor contained within the arm that is operated by the power supply to vibrate the arm with the flossing head attached thereto when the motor is activated. The activation of the motor is obtained when the flosser is in an unfolded position. While the activation may be achieved in many different ways, the preferred manner includes a first electrical contact in communication with the power supply and positioned in the handle, and a second electrical contact in communication with the motor and positioned in the arm such that when the flosser is in the unfolded position the first and second electrical contacts make an electrical connection whereby power from the power supply is able to operate the motor.

In another aspect of the invention, when the flosser is in a folded position, the electrical connection between the first and second electrical contacts is broken such that the motor turns off. The manner in which the motor moves the flossing head is defined by having an axle that has a weight secured in an offset position, such that when the offset weight is spun by the motor the end of the arm oscillates causing the flossing head to vibrate. In addition thereto, the flossing head can be removed such that worn floss material may be replaced and the flossing head may be manually rotated by the user such that the arm and flossing head can be stored in a cavity defined by the handle, when the flosser is in a folded position.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein:

FIG. 1 is a perspective view of an electric folding flosser illustrating the components through the outside cover of the flosser and illustrating the flossing in an unfolded position;

FIG. 2 is a perspective view of the razor in FIG. 1 illustrating the flosser in an partially folded position;

DETAILED DESCRIPTION OF THE EMBODIMENTS

Figure 3:
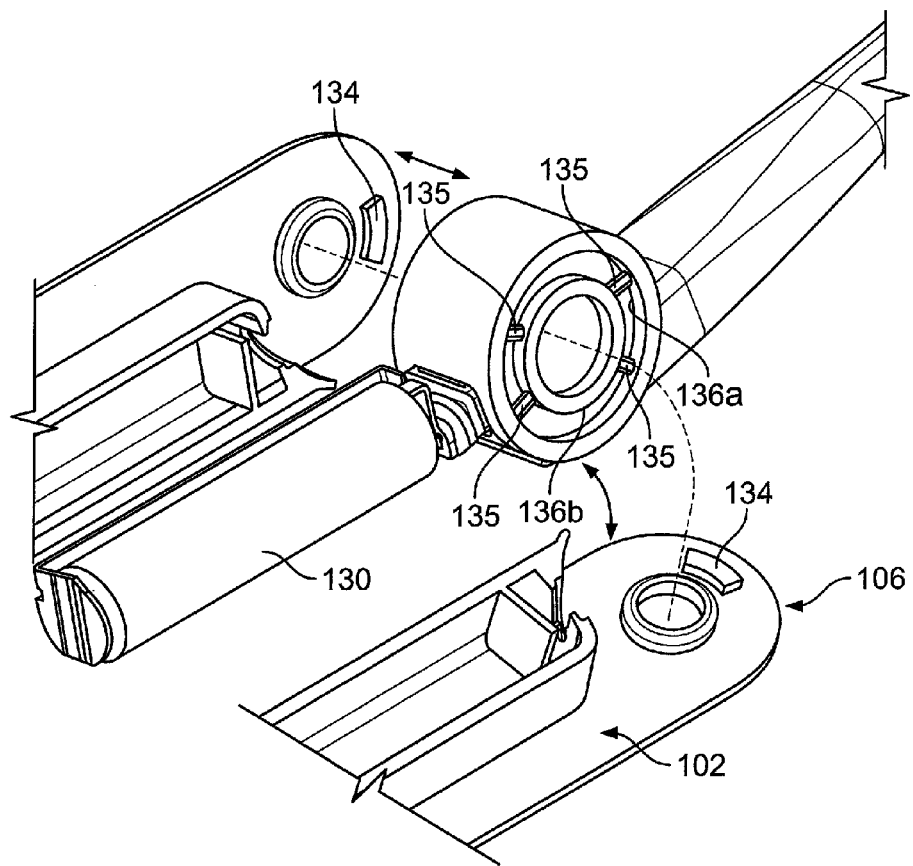
FIG. 3 is an enlarged perspective view of a mechanism that holds the flosser in an unfolded position.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Referring now to FIG. 1, in a first embodiment, an electric folding flosser is illustrated and generally referenced to as 100. The flosser includes a handle section 102 that a user grasps during use of the flosser 100. An arm section 104 is moveably attached to one end of the handle section 102. As illustrated in FIGS. 1 and 2, the pivotal region 106 permits the handle section 102 and the arm section 104 to pivot about the region 106 in such a manner that the flosser 100 may move from a substantially folded position to a substantially prone position.

Secured to the other end of the arm is a flossing tool 108 that is rotatably attached to the arm 104, such that the flossing tool 108 can be aligned along the same plane as the arm 104. As such, when the flosser 100 is in a folded position, the rotated flossing tool 108 and arm 104 are received within a cavity 110 defined by the handle 102.

The flosser includes a mechanical means to move the flossing tool 108. The mechanical means is preferably a motor 120 contained within the arm that rotates an axle 122 that includes a weight 124 that is secured to the axle 122 in an offset position. When the motor 120 is activated the offset weight 124 spins causing the arm 104 to vibrate and thus the flossing tool 108 will move as it is attached thereto. Other means for moving the flossing tool contemplated by this invention and covered by the aforementioned claims include having a motor that drives a gear train, which rotates or oscillates the flossing tool, such means are well known in the electric toothbrush industry.

To operate the present invention, a set of motor contacts 126 in electrical communication 127 with the motor will make an electrical connection with a set of power contacts 128 that are in electrical communication 129 with a power supply 130 or a battery. The flosser 100 houses the set of motor contacts 126 in the arm 104 about the pivotal region 106 and houses the set of power contacts 128 in the handle 102 about the pivotal region 106. The two sets of contacts 126 and 128 are exposed such that when the flosser 100 is in a substantially prone position, the two sets of contacts 126 and 128 will make an electrical connection, which provides power to the motor 120 (FIG. 2). In addition, to deactivate the motor 120 or break the electrical connection, the flosser 100 is moved from the substantially prone position to a folded position (FIG. 1).

Referring now to FIG. 3, the flosser 100 also includes a means to maintain the flosser 100 in an unfolded and folded position. The means to maintain the flosser 100 in a specific position is achieved by providing a pair of opposing detents 134 on the inside portion of the handle section 102 about the pivoting region 106. The detents 134 slide into recesses, defined between a plurality of ribs 135, on the arm section 104. When the flosser 100 is in an unfolded position and electrical contact is made between the two sets of contacts 126 and 128, the detents 134 are positioned in the first recess 136a. This helps to maintain the electrical connection during use of the flosser 100. When the flosser 100 is moved from the unfolded position, by pivoting the handle section 102 and arm section 104 towards each other, the detents 134 move out of the first recess 136a and into the secondary recesses 136b. While in this position, the detents 134 help prevent the flosser 100 from accidentally moving into the unfolded position, and thus inadvertently activating the flosser 100.

Also illustrated in FIGS. 1-3 the handle 102 preferably includes an end with a pair of opposing sides to define a gap there between. The arm 104 is movably joined between the opposing sides of the end of the handle 102, to define a moveable junction there between.

In addition, one end of the flosser 100 may also include a key ring 112 or other external attachment means for attaching the flosser 100 to the user's keys or for attaching the flosser to a zipper defined on a travel bag. This would help prevent the user from misplacing or forgetting the flosser 100.

Figure 4:
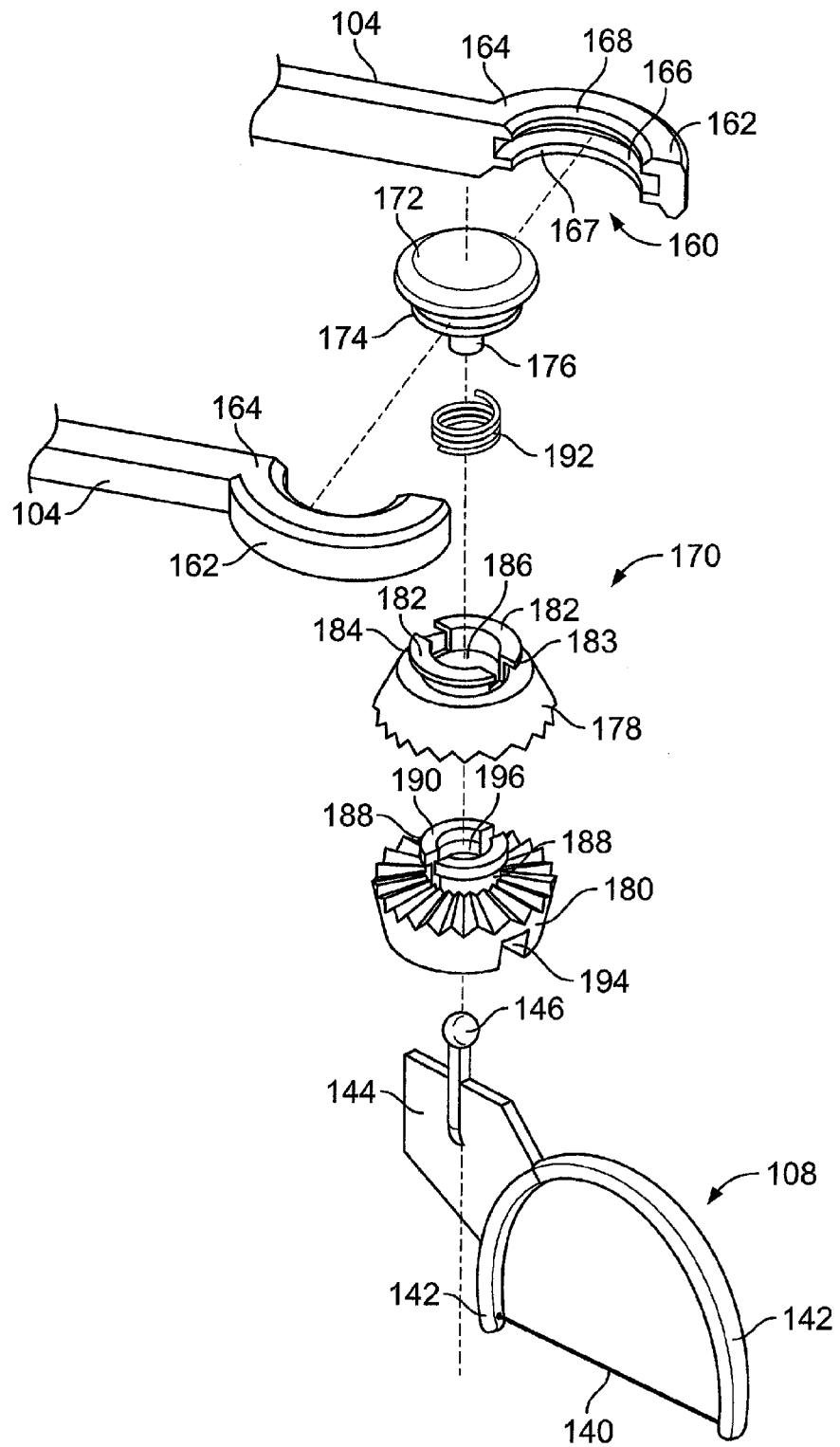
FIG. 4 is an exploded view of an ejector mechanism employed to releasably secure the flossing tool to the arm.
Figure 5:
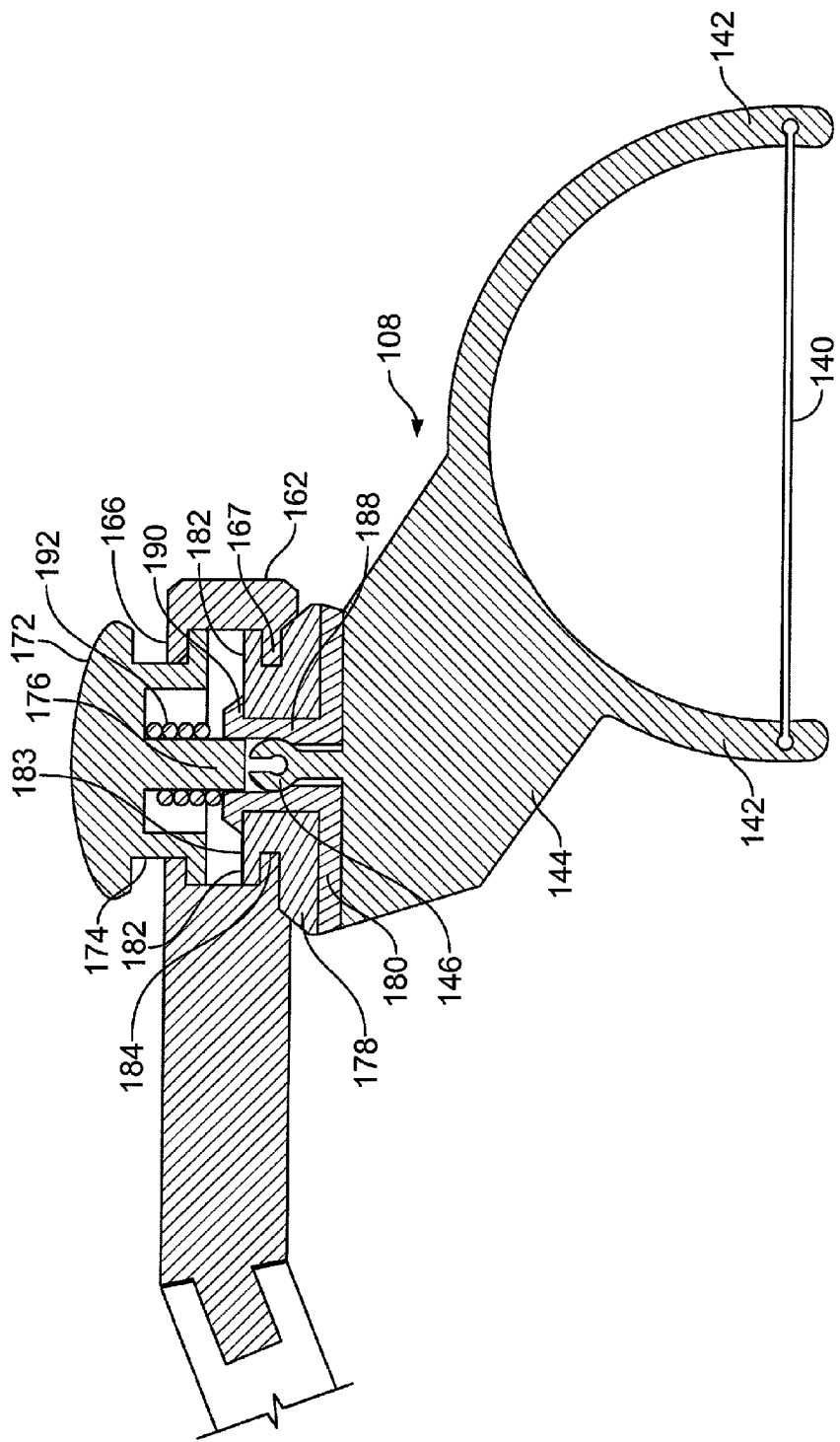
FIG. 5 is a cross section view of FIG. 4 when in the assembled position.

As mentioned above, the flossing tool 108 is rotatably and removably attached to the arm 104. This is accomplished by attaching the flossing tool 108 to the arm 104 via a rotatable ejector mechanism 170. Referring to the exploded view of FIG. 4 and the cross-section view of FIG. 5, the flossing tool 108 may be described as having a section of flossing material 140 stretched over a cavity that is created between two opposable arms 142, which extend in an arc from a support region 144. The support region 144 includes a knob 146 extended upwardly from the support region that frictionally fits into the bottom of ejector mechanism 170 (discussed in greater detail below) such that the flossing tool 108 may be held securely in place but also may be removed by the user.

Figure 6:
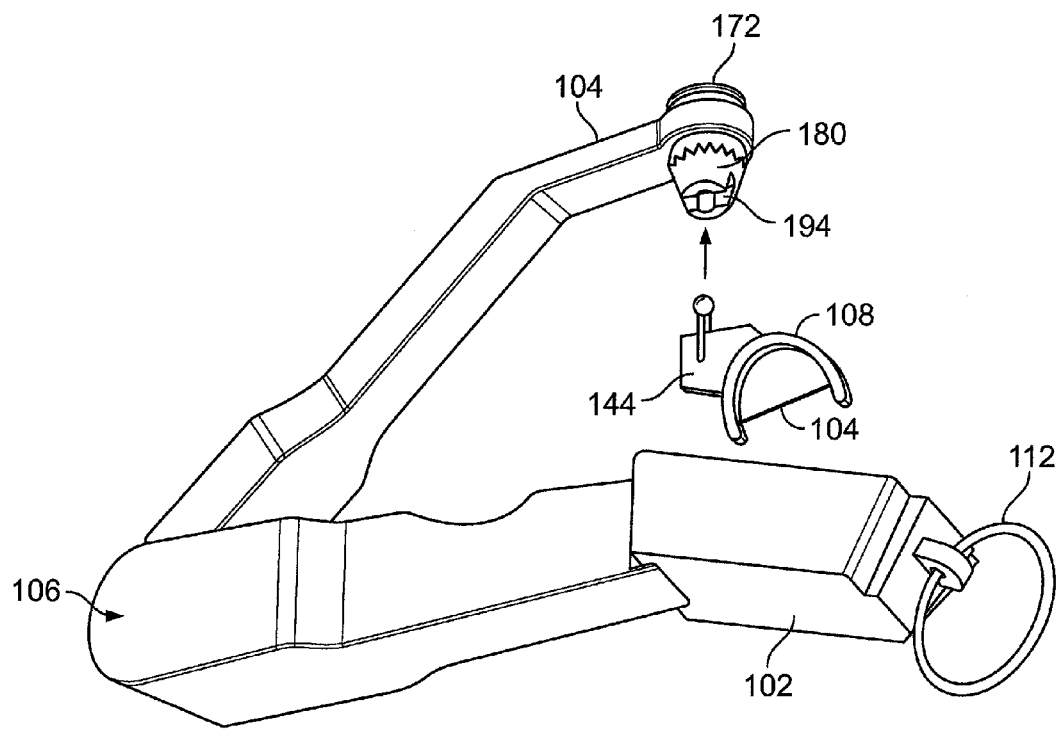
FIG. 6 is a perspective view of the flossing tool being attached to the ejector mechanism.

The ejector mechanism 170 has a head 172 that is secured to the arm 104 by positioning the head 172 in a circular cavity 160 that is created between two opposable arms 162 that extend in an arc from the end 164 of the arm 104. The head 172 includes a body 174 that receives an upper lip 166 defined on the interior wall 168 of the cavity 160. The head 172 also includes a pin 176 that extends downwardly from the bottom portion of the head 172. The ejector mechanism 170 includes a pair of interlocking face ratchets, a first face ratchet 178 and a second face ratchet 180. The first face ratchet 178 includes a pair of first face flanges 182 and has a C-shaped body 184. The first face flanges 182 are capable of flexing towards each other such that C-shaped flanges engages a bottom lip 167 defined on the interior wall 168 of the cavity 160. The first face ratchet 178 also includes a centered bore 186. The second face ratchet 180 includes a pair of second face flanges 188 with lips 190. The second face flanges 188 are positioned through the centered bore 186 of the first face ratchet 178 such that the lips 190 of the second face flanges 188 engage the top portion 183 of the first face flanges 182. The second face ratchet 180 further includes a groove 194 and a center bore 196 to receive the knob 146 of the flossing tool 108. A spring 192 is positioned between the head 172 and the lips 190 of the second face flanges 188 to bias the two away from each other. When the head 172 is pushed downwardly, the pin 176 on the head 172 moves through the center bore in the first and second face ratchets 178 and 180, respectively. The pin 176 will push against the knob 146 on the flossing tool 108 such that the knob 146 pushes out of the center bore 196 of the second face ratchet 180 and the flossing tool 108 is released. To insert the flossing tool 108, a user simply aligns the support region 144 with the groove 194 and pushes the knob 146 on the flossing tool 108 into the center bore 196 of the second face ratchet 180 (FIG. 6).

Figure 7:
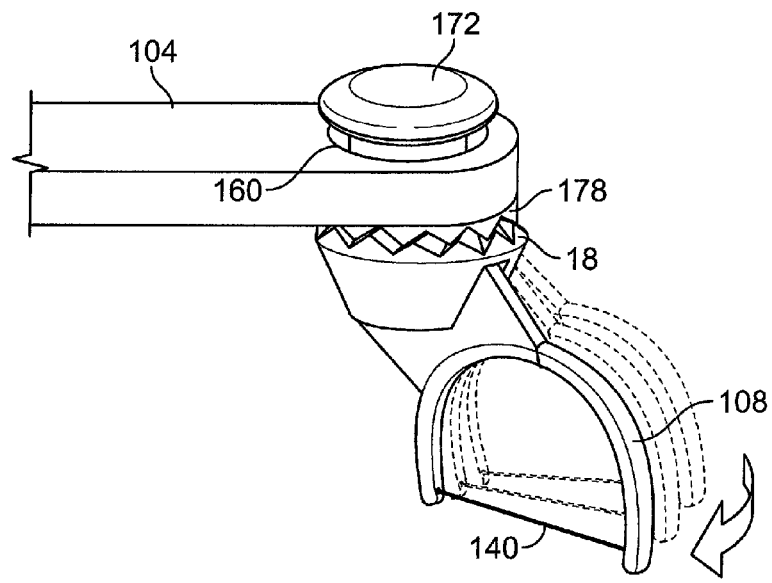
FIG. 7 is an enlarged perspective view illustrating the rotation of the flossing tool.

As illustrated in FIG. 7, the flossing tool 108 may be rotated with respect to the arm, by rotating the second face ratchet 180 with respect to the first face ratchet 178. The interconnecting teeth on the first and second face ratchets permit the flossing tool 108 to be locked into various angles in relation to the arm 104.

Figure 8A:
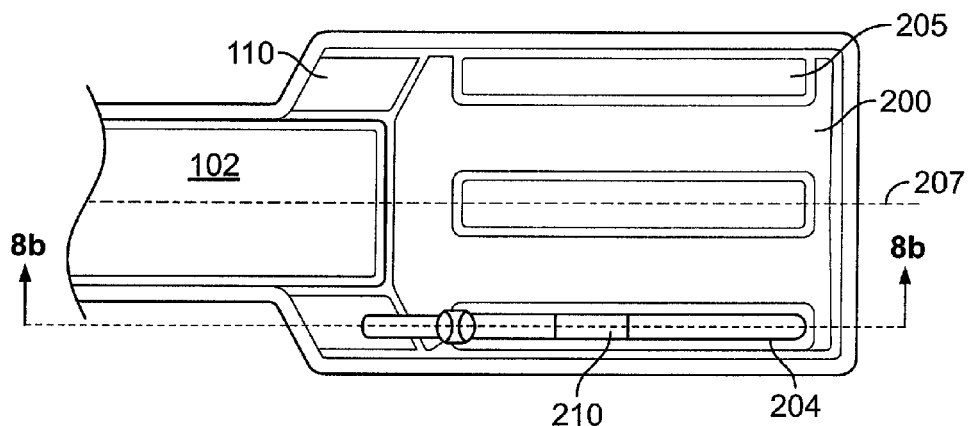
FIGS. 8a and 8b are top and side views respectively, illustrating a cavity that holds the flossing tool attached to the arm when the flosser is in a folded position and holds extra flossing tools.
Figure 8B:
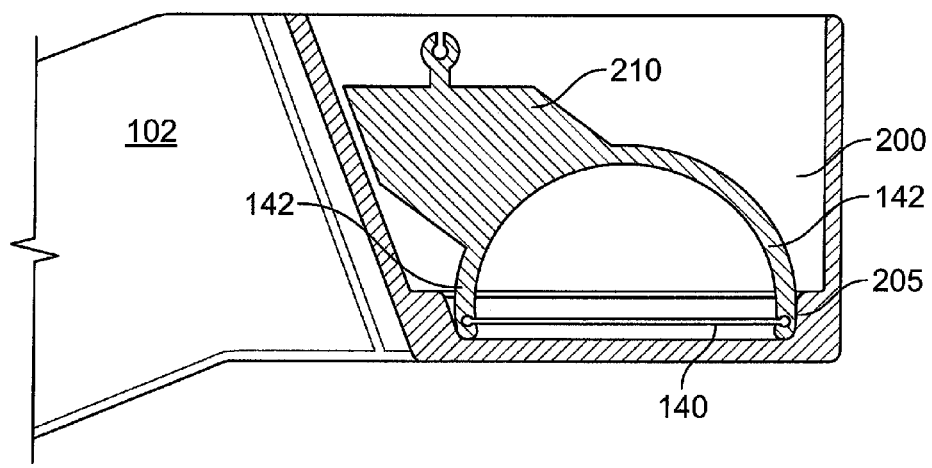

As mentioned above, when the flosser 100 is in a folded position and the flossing tool 108 is pivoted to align crosswise with the arm, the arm 104 and the flossing tool 108 are received in a cavity 110. Moreover, the cavity 110 is capable of holding extra flossing tools such that a user can store replacement flossing tools 210. As illustrated in FIGS. 8a and 8b, the cavity 110 includes an enlarged section 200 that has multiple slotted channels 205 sized to frictionally receive the ends of the two opposable arms 142 of the flossing tool. A centered channel 207 is positioned to receive the flossing tool 108 that is attached to the arm 104 of the flosser 100, when the flossing tool 108 is aligned such that the flossing member 140 is crosswise with the arm 104.

The first embodiment of the present invention may also simply provide for a folding flosser with the aforementioned ejector mechanism without a means to vibrate the flossing tool. Such a folding flosser with a cavity to provide for the flosser and extra disposable flossing tool is contemplated by the present invention.

Figure 9:
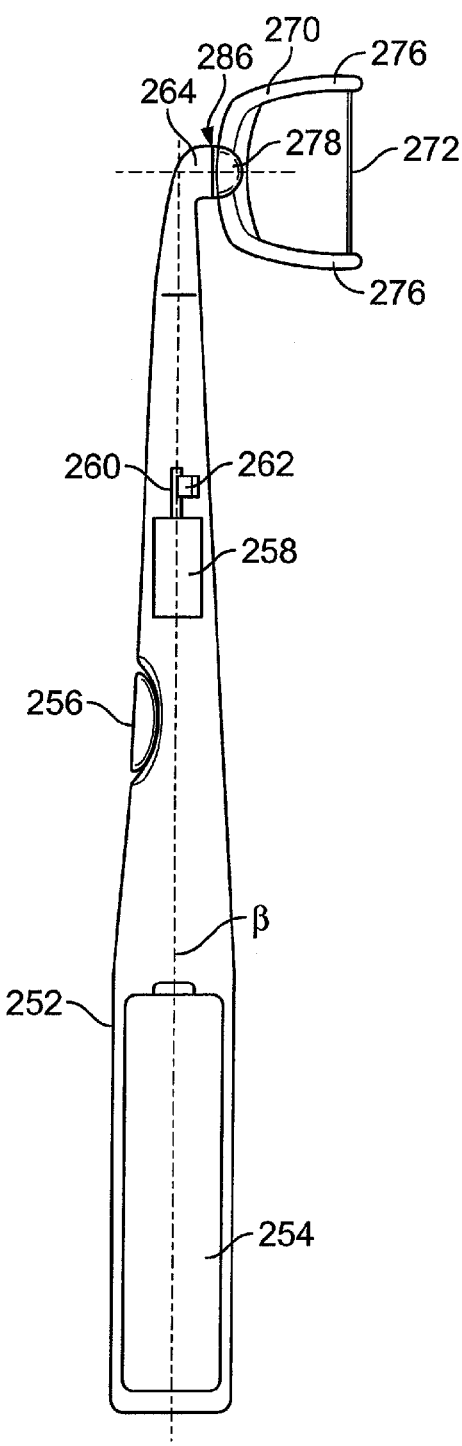
FIG. 9 is a side view of a second electric flosser in accordance with the present invention that includes a fully rotatable flossing tool.
Figure 10:
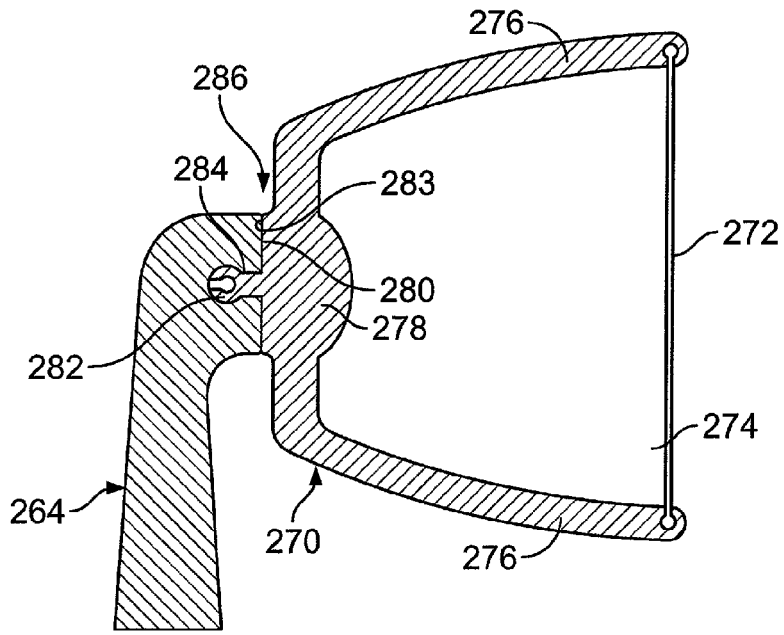
FIG. 10 is a cross sectional view of the flossing tool attached to the end of the electric flosser shown in FIG. 9.
Figure 11:
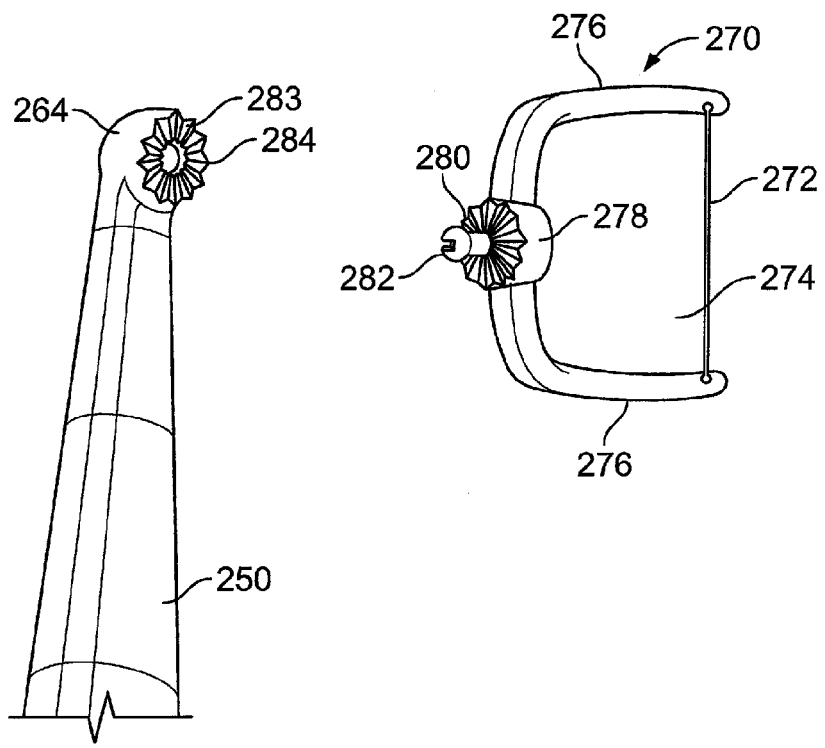
FIG. 11 is a perspective view showing the rotatable flossing tool and the end of the electric flosser.

Referring now to FIGS. 9-11, an electric flosser 250 in accordance with a second embodiment of the present invention is illustrated. The electric flosser 250 includes a handle 252 that houses a power supply, such as a battery 254. The power supply is electrically connected to a power controller, or one or more buttons 256, that controls the power to a motor 258. The motor 258 when turned on drives a shaft 260 that rotates a weight 262 that is offset from an axis β in the electric flosser 250. When the weight 262 is rotating about the axis β an end 264 defined by the handle 252 oscillates or vibrates about the axis β. Attached to the end 264 is a rotatable flossing tool 270.

Figures 12A, 12B:
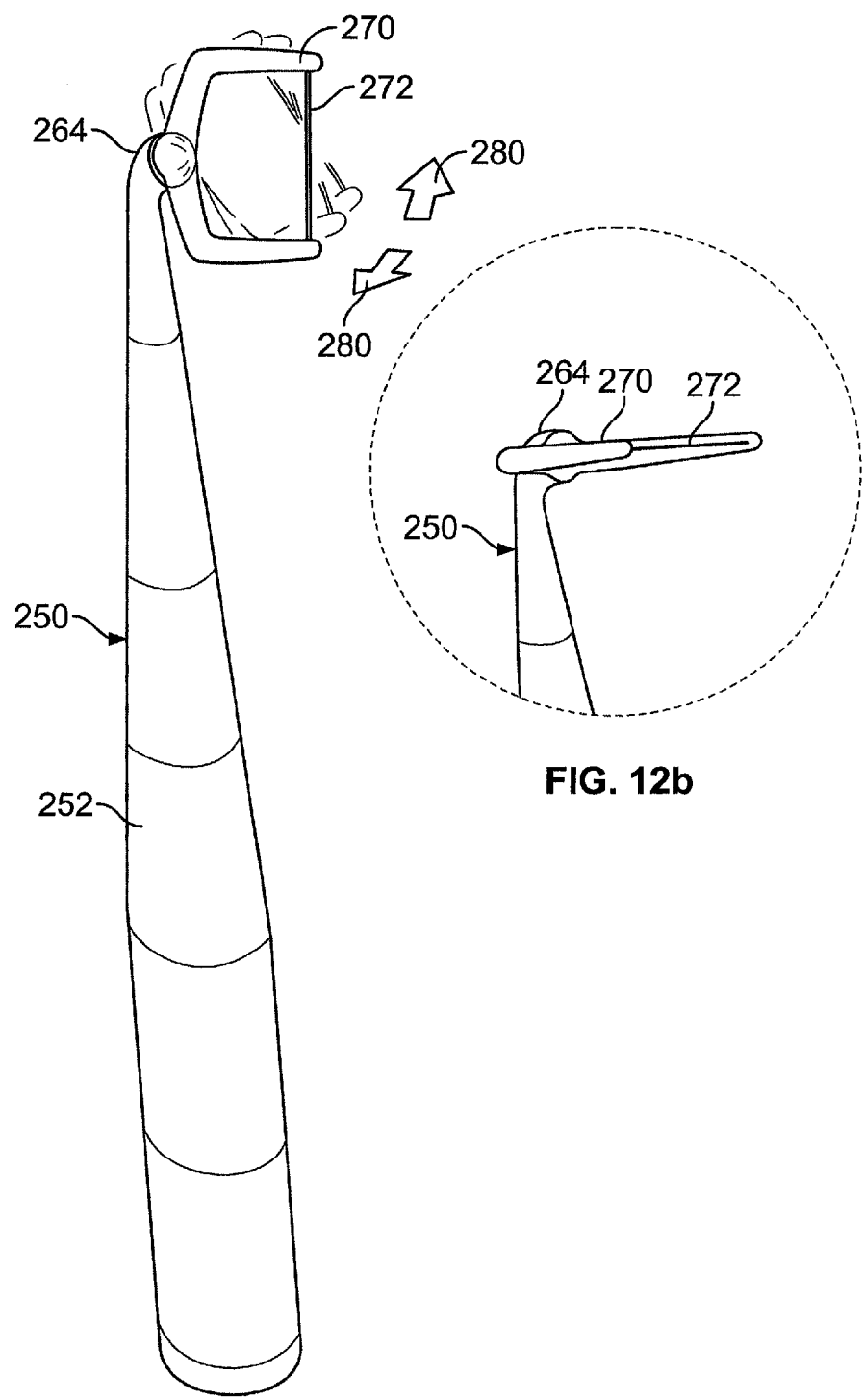
FIGS. 12a and 12b is a perspective view illustrating the vibration motion of the flossing tool when the flossing tool is rotated to different positions.

As best seen in FIG. 11, the flossing tool 270 has a section of flossing material 272 stretched over a cavity 274 that is created between two opposable arms 276, which extend in an arc from a support region 278. The support region 278 includes a circular ratchet face 280 with a knob 282 extending outwardly from the face 280. The end 264 of the flosser 250 includes a circular ratchet face 283 with an aperture 284 defined in the center thereof. The support region 278 mates with the end 264 of the flosser 250 by inserting the knob 282 into the aperture 284 wherein the circular ratchet face 280 of the support region mates with the circular ratchet face 283 of the end 264 to form an interlocking ratchet 286 that allows the flossing tool 270 to fully rotate 360°. The user simply rotates the flossing tool 270 to a desired angle (illustrated in FIGS. 12a and 12b) for use. Moreover, the interlocking ratchet 286 temporarily locks the flossing tool 270 in a desired position during use, thereby preventing the flossing tool 270 from rotating on its own.

Unlike the prior art, the flosser 250 in accordance with the second embodiment does not reciprocate the flossing material along an axis substantially parallel to the axis of a handle nor does the motor move a shaft in the handle along the handle's longitudinal axis.

From the foregoing and as mentioned above, it will be observed that numerous variations and modifications may be effected without departing from the spirit and scope of the novel concept of the invention. It is to be understood that no limitation with respect to the specific embodiments illustrated herein is intended or should be inferred. It is, of course, intended to cover by the appended claims all such modifications as fall within the scope of the claims.

I claim:

1. A flossing apparatus comprising:
   a handle;
   an arm movably joined to said handle and having a flossing tool disposed at one end thereof;
   a cavity provided in said handle sized to receive the arm and said flossing tool when the arm and handle are moved towards each other to a folded position; and
   a means to rotate said flossing tool with respect to said arm, wherein the means to rotate includes:
      an ejector mechanism that includes a head movably secured to the arm in a traverse direction, the head includes a pin extending outwardly;
      first and second ratchets that interlock to provide interlocking positions with respect to each other, the first ratchet secured to the arm below said head and the second ratchet rotatably secured to the first ratchet, both the first and second ratchets include a bore positioned to receive said pin, said bore in the second ratchet sized to frictionally receive a knob positioned on a top portion of the flossing tool, such that a flossing tool may be secured to the ejector mechanism;
      a spring positioned between the head and the first and second ratchets to bias the head away from the first and second ratchets;
      wherein when a flossing tool is secured to the second ratchet and the head is pushed downwardly the pin travels through the bore in the first and second ratchets and pushes the knob on the flossing tool out of engagement with the second ratchet such that the flossing tool is released.

2. The flossing apparatus of claim 1 further comprising:
   a power supply contained within the handle; and
   a mechanical means contained within the arm and operated by said power supply to create movement of the flossing tool when said mechanical means is activated.

3. The flossing apparatus of claim 2, wherein the power supply includes a first electrical contact and the mechanical means includes a second electrical contact and when the arm and handle are in an unfolded position, the first electrical contact makes an electrical connection with the second electrical contact to power the mechanical means.

4. The flossing apparatus of claim 3, wherein when the arm and handle are in a folded position, the electrical connection between the first and second electrical contacts is broken such that the mechanical means becomes disabled.

5. The flossing apparatus of claim 4, wherein the mechanical means to create movement of the flossing tool includes a motor mechanism and an offset weight that is spun about an axle that is rotated by the motor mechanism.

6. The flossing apparatus of claim 5 further comprising a means to maintain the arm and handle in said unfolded position.

7. The flossing apparatus of claim 6, wherein the means to maintain the arm and handle in said unfolded position includes a detent fixed on the handle about a region defined as where the arm is joined to the handle, said detent moves in relation to a first recess, of a plurality of recesses fixed on the arm about said region.

8. The flossing apparatus of claim 7, wherein the flossing tool is rotatably connected to the arm such that the flossing tool may be aligned crosswise with the arm, and said handle includes a cavity for receiving said arm and said flossing tool when said flossing tool is pivoted crosswise with said arm and when said arm and handle are in a folded position.

9. The flossing apparatus of claim 8, wherein the cavity includes an enlarged section to receive the flossing tool and includes slotted channels sized to frictionally receive additional flossing tools.

10. A flossing apparatus comprising:
    a handle having a power supply contained therein, and having an end with a pair of opposing sides positioned to define a gap there between;
    an arm movably joined between said opposing sides of said end of the handle, to define a movable junction there between and having a flossing tool rotatably connected at one end of said arm;
    a motor mechanism contained within the arm and operable to move said flossing tool when activated; and a means for supplying power to the motor mechanism when the arm and handle are in an outstretched position, wherein the rotatable connection between the flossing tool and the arm is defined by an ejector mechanism that includes a head removably secured to the arm in a transverse direction, the head includes a pin extending downwardly, first and second ratchets that interlock to provide interlocking positions with respect to each other, the first ratchet secured to the arm below said head and the second ratchet rotatably secured to the first ratchet, both the first and second ratchets include a bore positioned to receive said pin, said bore in the second ratchet sized to frictionally receive a knob positioned on a top portion of the flossing tool, such that a flossing tool may be secure to the ejector mechanism, and a spring positioned between the head and the first and second ratchets to bias the head away from the first and second ratchets, wherein when a flossing tool is secured to the second ratchet and the head is pushed downwardly the pin travels through the bore in the first and second ratchets and pushes the knob on the flossing tool out of engagement with the second ratchet such that the flossing tool is released.

11. The flossing apparatus of claim 10, wherein the means for supplying power to the motor mechanism when the arm and handle are in said outstretched position includes a first electrical contact in communication with the power supply and positioned in the handle, and a second electrical contact in communication with the motor mechanism and positioned in the arm such that when the arm and the handle are in said outstretched position the first and second electrical contacts make an electrical connection whereby power from the power supply is able to operate the motor mechanism.

12. The flossing apparatus of claim 11, further comprising a weight attached to an axle that is rotated by the motor mechanism, the weight is positioned on the axle such that when the axle is rotated the spinning weight causes the arm to oscillate such that the flossing tool vibrates.

13. The flossing apparatus of claim 10 further comprising:
a region defined about the movable junction of the arm and the handle;
a detent fixed on the arm about said region;
a first recess, of a plurality of recesses, fixed on the handle about said region;
wherein the arm and handle are maintained in an outstretched position when said detent moves into said first recess.

14. The flossing apparatus of claim 13, wherein the arm and handle are maintained in a position other than the outstretched position when the detent is moved into one of the plurality of recesses other than said first recess.

15. The flossing apparatus of claim 10 further comprising a cavity positioned in the handle sized to receive said arm and said flossing tool when the handle and the arm are in a folded position.

16. The flossing apparatus of claim 15, wherein the cavity includes a first slotted channel centered and positioned about the end of the cavity sized to receive said flossing tool attached to said arm and the cavity includes a second slotted channel offset from said first slotted channel and sized to receive a second flossing tool that is interchangeable with said first flossing tool.

17. An electric flossing apparatus having an end and a motor mechanism that when activated moves said end, further comprising:
a first ratchet face defined by said end of the apparatus and having an aperture defined therein; and
a flossing tool having a second ratchet face to coact with the first ratchet face, the flossing tool having a knob extending on a rod outwardly from a center portion of the second ratchet face and sized to frictionally engage the aperture positioned in the first ratchet face such that when the flossing tool is attached to the end of the apparatus, the flossing tool is rotatably secured thereto, and wherein the knob is further defined as having two halves spaced apart from one another to define an opened region there between such that the flossing tool is both frictionally engaged to and removable from the apparatus.

18. The electric flossing apparatus of claim 17 wherein the motor rotates an offset weight that causes the end of the apparatus to oscillate.

19. The electric flossing apparatus of claim 18 further comprising a means to control the activation of the motor.

20. A flossing apparatus comprising:
a handle housing a means to supply power to a motor, the motor rotates an offset weight that causes an end of the apparatus to oscillate, the end having a ratchet face and an aperture in the center of said face;
a flossing tool having a support region with a ratchet face and a knob extending outwardly on a rod from the ratchet face, the knob further has two halves spaced apart from one another to define an opened region there between such that the flossing tool is sized to frictionally engage and be removable from the aperture,
wherein when the knob is engaged with the aperture, the ratchet face defined by the support region mates with the ratchet face defined by the end of the apparatus to form an interlocking ratchet that permits the flossing tool to rotate with respect to the end of the apparatus.

* * * * *